United States Patent
Adams et al.

(10) Patent No.: US 12,144,720 B2
(45) Date of Patent: Nov. 19, 2024

(54) ROTATOR CUFF CABLE RECONSTRUCTIONS

(71) Applicant: Arthrex, Inc., Naples, FL (US)

(72) Inventors: Christopher R. Adams, Naples, FL (US); Matthew R. Herrington, Naples, FL (US); Justina M. Heidenthal, Naples, FL (US)

(73) Assignee: Arthrex, Inc., Naples, FL (US)

( * ) Notice: Subject to any disclaimer, the term of this patent is extended or adjusted under 35 U.S.C. 154(b) by 278 days.

(21) Appl. No.: 17/390,106

(22) Filed: Jul. 30, 2021

(65) Prior Publication Data

US 2023/0035089 A1    Feb. 2, 2023

(51) Int. Cl.

| A61F 2/08 | (2006.01) |
|---|---|
| A61B 17/04 | (2006.01) |
| A61B 17/16 | (2006.01) |
| A61B 17/32 | (2006.01) |
| A61B 17/56 | (2006.01) |
| A61F 2/40 | (2006.01) |

(52) U.S. Cl.
CPC ......... *A61F 2/0811* (2013.01); *A61B 17/0483* (2013.01); *A61F 2002/0852* (2013.01); *A61F 2210/0004* (2013.01); *A61F 2220/0075* (2013.01)

(58) Field of Classification Search
None
See application file for complete search history.

(56) References Cited

U.S. PATENT DOCUMENTS

| 5,681,333 A | 10/1997 | Burkhart et al. | |
|---|---|---|---|
| 6,716,234 B2* | 4/2004 | Grafton | C08L 23/06 606/228 |
| 7,001,411 B1* | 2/2006 | Dean | A61B 17/0401 606/220 |
| 7,303,577 B1* | 12/2007 | Dean | A61B 17/0643 606/151 |
| 7,967,820 B2* | 6/2011 | Bonutti | A61B 17/7233 606/64 |
| 8,652,173 B2* | 2/2014 | Mansmann | A61F 2/30756 606/232 |
| 8,690,915 B2 | 4/2014 | Hootstein | |
| 9,271,722 B2 | 3/2016 | Cournoyer et al. | |
| 9,615,821 B2 | 4/2017 | Sullivan | |
| 9,693,765 B2 | 7/2017 | Sullivan et al. | |

(Continued)

OTHER PUBLICATIONS

International Search Report and Written Opinion for International Application No. PCE/US2022/028772, Dated Aug. 16, 2022.

(Continued)

*Primary Examiner* — Ann Schillinger

(74) *Attorney, Agent, or Firm* — Potomac Law Group, PLLC

(57) ABSTRACT

Surgical constructs, assemblies, and methods for rotator cable reinforcement with a flexible coupler and an optional reinforcement material. The rotator cable between the attachment points is reinforced with a suture in different configurations. The anchor points are located at the insertion sites of the rotator cable and a continuous stitch reinforces the rotator cable. The continuous stitch bridges the cable footprint insertion points, to displace forces from the rotator cuff tendon.

12 Claims, 3 Drawing Sheets

(56) References Cited

U.S. PATENT DOCUMENTS

| | | | |
|---|---|---|---|
| 9,707,069 B2* | 7/2017 | Kumar | A61F 2/0811 |
| 10,568,733 B2* | 2/2020 | Park | A61F 2/08 |
| 10,575,842 B2* | 3/2020 | Lund | A61L 31/048 |
| 10,849,734 B2* | 12/2020 | Holowecky | A61B 17/0485 |
| 10,932,770 B2 | 3/2021 | Stone et al. | |
| 10,966,814 B2* | 4/2021 | Hansen | A61B 17/56 |
| 2006/0079904 A1 | 4/2006 | Thal | |
| 2007/0219558 A1* | 9/2007 | Deutsch | A61B 17/0401 606/326 |
| 2008/0188936 A1* | 8/2008 | Ball | A61F 2/08 623/13.13 |
| 2008/0262544 A1* | 10/2008 | Burkhart | A61B 17/0401 606/228 |
| 2009/0036905 A1 | 2/2009 | Schmieding | |
| 2011/0125287 A1* | 5/2011 | Hotter | A61F 2/0063 606/228 |
| 2012/0265219 A1* | 10/2012 | Rushdy | A61B 17/0401 606/139 |
| 2014/0135834 A1* | 5/2014 | Mansmann | A61B 17/0401 606/232 |
| 2015/0216522 A1 | 8/2015 | Ticker | |
| 2016/0345954 A1* | 12/2016 | Marino | A61F 2/0811 |
| 2017/0049432 A1 | 2/2017 | Dooney et al. | |
| 2018/0206977 A1* | 7/2018 | Park | A61F 2/0811 |
| 2021/0100546 A1* | 4/2021 | Schmieding | A61B 17/0401 |
| 2022/0287705 A1* | 9/2022 | Sengun | A61B 17/06166 |
| 2023/0338019 A1* | 10/2023 | Dooney, Jr. | A61B 17/04 |
| 2024/0074745 A1* | 3/2024 | Petry | A61B 17/06166 |
| 2024/0164770 A1* | 5/2024 | Chao | A61B 17/06166 |

OTHER PUBLICATIONS

Wieser et al., "Stitch positioning influences the suture hold in supraspinatus tendon repair," Knee Surgery, Sports Traumatology, Arthroscopy, 2013, vol. 12, pp. 1587-1592.

\* cited by examiner

ROTATOR CUFF CABLE RECONSTRUCTIONS

BACKGROUND

The disclosure relates to the field of surgery and, more specifically, to surgical constructs and tissue repairs for reconstructive surgeries.

SUMMARY

Knotless, high-strength surgical constructs and methods of tissue repairs are disclosed.

A surgical construct can include a rotator cable with a flexible coupler extending along at least a portion of a length of the rotator cable located between its natural insertion points. A flexible coupler can include at least one flexible strand located around and/or through the rotator cable and forming one or more suturing passes around the rotator cable, to stitch up the rotator cable and reinforce it. A surgical construct can include at least one fixation device for providing at least one anchoring point of the rotator cable. A surgical construct can include one or more reinforcement materials to aid the flexible coupler in reinforcing the rotator cable. A surgical construct can be knotless, self-locking and tensionable.

Methods of knotless, self-locking and tensionable tissue repairs are also disclosed. A surgical construct provides knotless tissue to bone fixation, without knot formation, with increased fixation and improved healing, and uniform soft tissue compression. A tissue can be rotator cable of the rotator cuff tendon.

DETAILED DESCRIPTION

Figure 1:
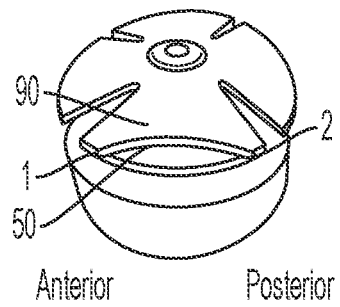
FIGS. 1-5 illustrate steps of a tissue repair.

The disclosure provides knotless, tensionable surgical systems, assemblies, constructs, and methods for tissue repairs and reconstructions, employing tissue reinforced with a flexible coupler and optionally a reinforcement (reinforcing) material such as suture, tape, weave, or mesh, among many others. The tissue can be the rotator cable of the rotator cuff tendon. The tissue can be reinforced with the flexible coupler alone or in combination with a reinforcement material (which in turn can be employed alone, or in combination with any additional biological construct, for example, graft, collagen, collagen patch, biological materials). The reinforced rotator cable can be attached to any fixation device(s), for example, knotless suture anchors.

A surgical construct can include a rotator cable stitched with a flexible coupler. The flexible coupler can be suture or tape. The flexible coupler is provided around or through the rotator cable (or both around and through the rotator cable) by forming a stitched region including one or more suture passes around the rotator cable. A surgical construct can be knotless, self-reinforcing, tensionable, adjustable. The flexible coupler can be suture or suture tape.

A surgical assembly or surgical system can include a rotator cable; a flexible coupler provided around and/or through the rotator cable in a suturing/stitched configuration; and at least one fixation device attached to the flexible coupler. The surgical assembly can optionally include a reinforcement material (a piece of material) provided along at least one dimension (for example, the length or height) of the rotator cable, to aid in providing a reinforced rotator cable. The fixation device can be an anchor, button, implant, screw, plate, suture loop/button construct, or combinations thereof. The fixation device can be a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein. A knotless fixation device comprises an anchor body (or screw) and an eyelet.

A reinforced rotator cable construct can include a sutured or stitched region formed by employing (1) a flexible coupler; and conducting (2) at least one pass around and/or through the rotator cable. The step of conducting (2) at least one pass around and/or through the rotator cable could take place after or before or during a piece of reinforcement material has been attached/affixed or is being attached/affixed to the footprint of the rotator cable. The flexible coupler can be passed around and/or through at least a portion of the rotator cable to reinforce the cable. The flexible coupler can be attached to the rotator cable by suturing (for example, stitching such as whipstitching) or by any other affixing/attachment techniques, to provide additional reinforcement. A reinforced rotator cable construct can further include an additional reinforcing/reinforcement material, which can be any reinforcement or reinforcing material such as suture, tape, weave, ribbon, textile, or mesh that can be attached (sutured, stitched or passed around) to the cable. The reinforced rotator cable construct and/or the additional reinforcing/reinforcement material can be attached to additional fixation devices such as knotless anchors, among many others. The fixation devices can provide additional fixation to bone. The reinforced cable construct can be knotless, self-locking, tensionable.

Methods of forming knotless, reinforced rotator cable constructs having increased pull-out strength as well as methods of reinforcing a rotator cable are also disclosed. An exemplary method of forming a knotless, reinforced rotator cable construct (reinforced rotator cable) comprises: (i) suturing or stitching a rotator cable with at least one flexible coupler to form a reinforced rotator cable; and (ii) fixating the reinforced rotator cable with at least one fixation device. The at least one flexible coupler can be any strand or fiber that can allow suturing/stitching around an outer perimeter of the rotator cable and along at least one dimension of the rotator cable (for example, along its length or longitudinal axis). The at least one flexible coupler can be also passed through at least a portion of the rotator cable. The at least one flexible coupler can be suture or suture tape, among many others. The fixation device can be a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein.

The surgical constructs provide simplified, knotless, suturing systems and novel ways to repair large soft tissue tears where only certain attachment points are fixated back to bone. The tissue between the attachment points is reinforced with a suture in different configurations. The disclosure provides a technique wherein the anchor points are located at the insertion sites of the rotator cable and wherein a continuous stitch reinforces the rotator cable. The continuous stitch bridges the cable footprint insertion points, to displace forces from the rotator cuff tendon. The disclosure provides knotless fixation of rotator cable to bone, without knot formation, with fewer passing steps, increased fixation and reinforcement, uniform rotator cable compression, and overall rotator cuff rehabilitation and repair.

Figure 4:
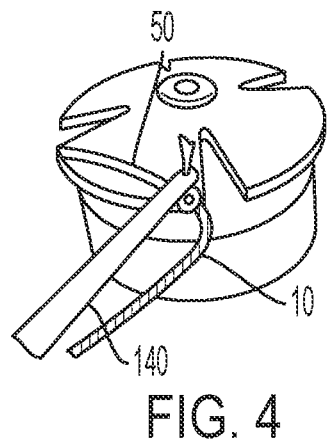
Figure 5:
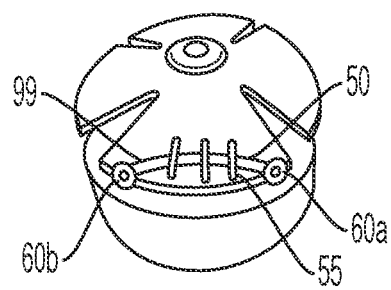
Figure 7:
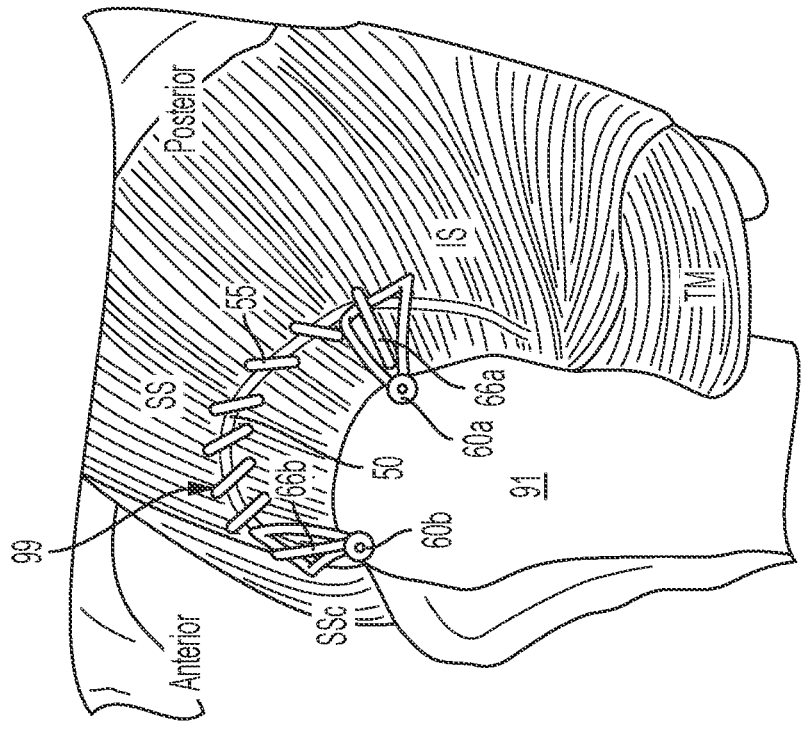
FIGS. 6-7 illustrate additional views of a reinforced tissue construct.
Figure 6:
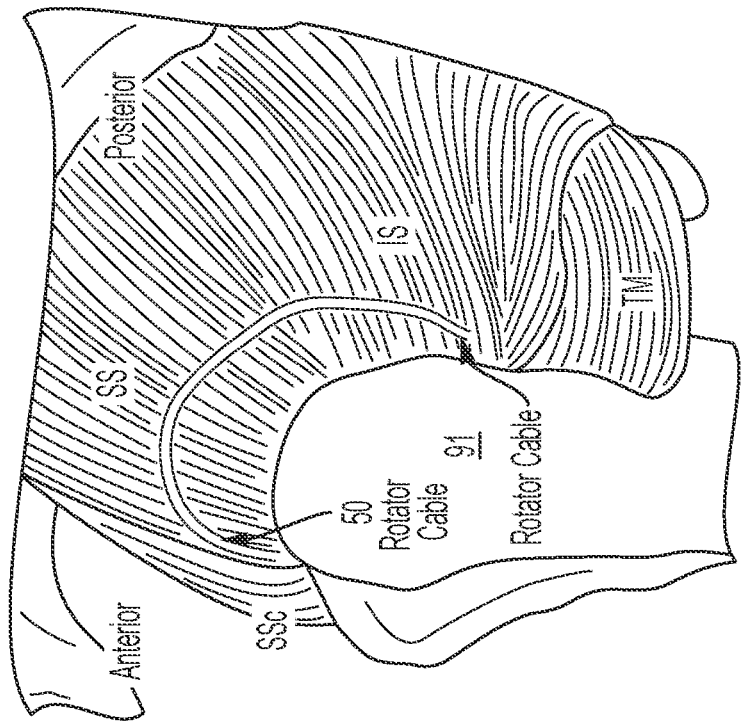
Figure 8:
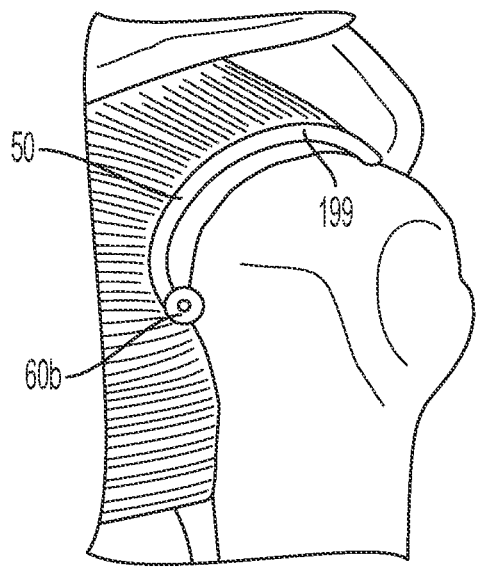
FIGS. 8 and 9 illustrate steps of a tissue repair according to another embodiment.
Figure 9:
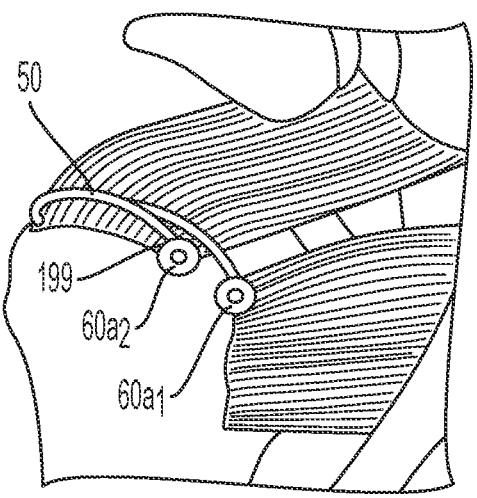

Referring now to the drawings, where like elements are designated by like reference numerals, FIGS. 1-9 illustrate exemplary surgical constructs 99, 199 (reinforced rotator cable constructs 99, 199; reinforced rotator cable 99, 199) and methods of forming surgical constructs 99. FIGS. 1-5 illustrate schematic steps of an exemplary method of forming a reinforced rotator cable 99. FIGS. 6 and 7 illustrate additional views of a reinforced tissue construct 99. FIGS. 8 and 9 illustrate steps of a tissue repair according to another embodiment.

FIG. 1 illustrates a schematic rotator cable 50 located over rotator cuff tendon 90 (rotator cuff 90), having two natural insertion points 1, 2 (anterior insertion point 1 and posterior insertion point 2).

Figure 2:
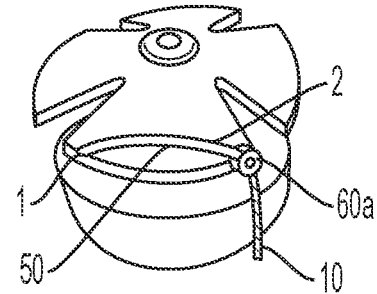

FIG. 2 illustrates placement of a first fixation device 60a with at least one flexible coupler 10 at the posterior insertion point 2. In an exemplary embodiment, first fixation device 60a can be an anchor (knotted anchor, knotless anchor, or all-suture anchor), implant, button, screw or any fixation device that confers secure attachment and fixation of the rotator cable 50 at the posterior anchoring point, to recreate the natural posterior anchoring point of the rotator cable. The fixation device 60a can be a knotless suture anchor such as a two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of both of which are fully incorporated by reference in their entirety herein.

At least one flexible coupler 10 can be placed in locking configuration and incorporated with anchor placement. Flexible coupler 10 can be formed of any flexible material. In an embodiment, flexible coupler 10 is round suture. In an embodiment, flexible coupler 10 is FiberWire® suture. In an embodiment, flexible coupler 10 is a tape such as suture tape. In an embodiment, flexible coupler 10 is FiberTape® suture tape. In an embodiment, flexible coupler 10 can consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. Flexible coupler 10 can consist of one or more strands with cross-sections of various forms and geometries, including round, oval, rectangular, or flat, among others, or combinations of such forms and geometries. In an embodiment, flexible coupler 10 can be provided as a suture which is braided, knitted or woven. Flexible coupler 10 can be partially or fully absorbable.

Figure 3:
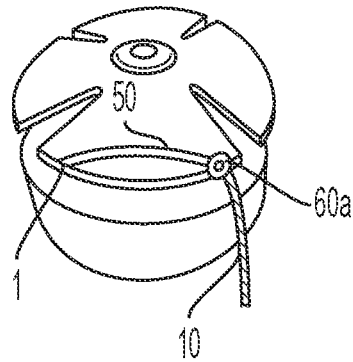

FIGS. 3 and 4 illustrate the step of passing flexible coupler 10 around rotator cable 50 to form at least one suture loop or stitch around the rotator cable 50, to reinforce the rotator cable. It can be understood, however, that the flexible coupler 10 can also go around or through the rotator cable 50, or both around and through it. A suture passer 40 (suture passing instrument) such as Arthrex Scorpion™ Suture Passer or Arthrex SutureLasso™ may be employed to pass flexible coupler 10 (suture 10) around the rotator cable, reinforcing the cable 50. In the illustrative embodiment, the flexible coupler 10 is passed around the outer circumference (outer perimeter) of the rotator cable 50, to reinforce it without piercing it.

FIG. 5 shows three complete stitches with flexible coupler 10 to form exemplary suturing pattern 55 (for example, running baseball stitch pattern 55). Multiple suturing methods may be achieved by integrating the coupler 10 in the final repair (e.g., whipstitch, rip-stop, Krackow, baseball, loop and tack, Bunnell, Kessler, Bauer, Strobel, etc. repairs). Suturing pattern 55 may have any configuration and pattern as long as the rotator cable 50 is reinforced along at least a length of one or more of its dimensions, for example, along the length or longitudinal direction of the cable, with the flexible coupler 10. A plurality of suturing passes can be provided from the posterior insertion/anchoring point 2 towards the anterior insertion/anchoring point 1, and reaching or about reaching the anterior insertion/anchoring point 1. The suturing/stitching can be achieved from any direction and towards any insertion/anchoring point 1, 2.

FIG. 5 illustrates placement of second fixation device 60b incorporating the repair suture 10 (flexible coupler 10) to anchor the anterior point 1 of the repair construct and form reinforced rotator cable 99 (surgical construct 99). In an exemplary embodiment, second fixation device 60b can be an anchor (knotted anchor, knotless anchor, or all-suture anchor), implant, button, screw or any fixation device that confers secure attachment and fixation of the rotator cable 50 at the anterior insertion point 1, to recreate the anterior insertion point 1 of the rotator cable 50. Fixation device 60b can be a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein.

Reinforced rotator cable 99 is formed by employing at least one flexible strand or coupler 10 to form at least one suture loop pass around the rotator cable 50. FIG. 7 shows stitched/sutured/reinforced region 55 of the reinforced rotator cable 99 which includes a plurality of full suture passes/stitches around an outer circumference of the rotator cable 50. The stitched/sutured/reinforced region 55 may be formed in any manner, by conducting a plurality of suture passes from posterior to anterior (i.e., in a direction from the second fixation device 60b with posterior insertion point 2 and towards the first fixation device 60a with anterior insertion point 1), or anterior to posterior (i.e., in a direction from the first fixation device 60a with anterior insertion point 1 and towards the second fixation device 60b with posterior insertion point 2). The stitched/sutured/reinforced region 55 may include any number of passes or stitches placed along at least a length of the rotator cable 50. In an exemplary embodiment, a plurality of passes or stitches are placed along about the whole length of the rotator cable 50, and in a direction about parallel to the longitudinal axis of the rotator cable.

The stitched/sutured/reinforced region 55 may be also formed by passing at least one flexible coupler 10 around the outer perimeter of the rotator cable 50 and/or through the rotator cable 50. In an embodiment, multiple flexible couplers 10 (strands such as suture or suture tapes or combinations thereof) are passed only around the outer perimeter of the rotator cable 50 to form a reinforced cable region 55 including a plurality of suture loop passes. In another embodiment, multiple flexible couplers 10 (strands such as suture or suture tapes or combinations thereof) are passed around the outer perimeter of the rotator cable 50 and also through the rotator cable 50, to form a reinforced cable region 55 including a plurality of suture loop passes.

FIGS. 6 and 7 illustrate additional views of the rotator cable 50 (FIG. 6) which undergoes a reconstruction/reinforcement technique of the present disclosure. FIG. 7 shows two exemplary fixations devices 60a, 60b which are two exemplary Arthrex SwiveLock® anchors 60a, 60b, fixed to the greater tuberosity 91. Each anchor is provided with two tails and one limb (flexible coupler 10) which forms stitched/sutured/reinforced region 55. FIG. 7 also shows additional suturing regions 66a, 66b corresponding to the fixation devices 60a, 60b in a rip-stop pattern and by a SpeedFix™ or SpeedBridge™ (not shown) configuration. The SpeedFix™ and SpeedBridge™ techniques, both developed by Arthrex, Inc., use a threaded swivel anchor 60a, 60b, such as Arthrex SwiveLock® C anchor (disclosed and described in U.S. Pat. No. 8,012,174) combined with FiberTape® (disclosed in U.S. Pat. No. 7,892,256) to create a quick and secure SpeedFix™ construct (a knotless single row repair) or a SpeedBridge™ construct (a knotless double row repair) with no knots and very few suture passing steps.

In the SpeedFix™ technique, FiberTape® suture is passed in an inverted mattress using a SutureLasso™ or Scorpion™ suture passer. The two suture limbs of the mattress stitch can then be inserted into the SwiveLock® anchor eyelet. The loaded eyelet is inserted into a prepared lateral bone socket until the anchor body contacts bone, and the tension is adjusted if necessary. The SwiveLock® C driver is rotated in a clockwise direction to complete the insertion. Using an open ended FiberWire® cutter, the FiberTape® tails are cut to complete the technique.

The above-described steps may be conducted on a left or right shoulder in an open or arthroscopic technique. In an arthroscopic technique, the patient would be positioned in a lateral decubitus or beach chair position and a 30 or 70 degree arthroscope is used for visualization. Two limbs of free suture tape are passed through the posterior rotator cable 50 and a second suture tape is passed through the tissue twice in a circumferential baseball stich configuration. The two limbs of the first suture tape and one shortened limb of the other suture tape have been secured with a suture anchor to the greater tuberosity. The rotator cable can be reinforced with a circumferential running baseball stitch and reconstructed with two SpeedFix™ suture configurations to reestablish the anterior and posterior cable attachments (insertion points 1, 2).

Exemplary steps of a surgical technique of forming a reinforced rotator cable construct 99 are as follows:
Rotator Cable Reinforcement and Reconstruction Technique for Irreparable Rotator Cuff Tear—Surgical Technique Patient positioning in the operating room can be based on surgeon's preference, in either the lateral decubitus or beach chair position. Diagnostic arthroscopy can begin with introduction of the arthroscope through a standard posterior portal into the glenohumeral joint. The technique can also be performed through an open surgical approach based on surgeon's preference. The rotator cuff tendon is evaluated intraarticularly to identify the extent of the tear anterior to posterior. Through the same posterior portal, the arthroscope is moved to the subacromial space. Standard anterior and lateral portals are created and a bursectomy may be performed to achieve visualization. Once the tear has been identified and rotator cuff tendon mobilization is performed, the tissue is assessed to determine whether it can be reduced back to the anatomic footprint. If mobility of the tissue precludes transosseous equivalent repair over the greater tuberosity, the rotator cuff tendon could be deemed to be irreparable and rotator cable reinforcement and reconstruction is performed.

The anterior and posterior limits of the rotator cable are identified with the arthroscope in the posterior portal. Through a lateral portal, suture such as Arthrex FiberTape® suture tape is passed through the posterior aspect of the rotator cuff tendon medial to the posterior cable and cable attachment site with a suture passer, such as the Arthrex Scorpion™ suture passer, from deep to superficial. The opposite limb of suture tape is passed again from deep to superficial, leaving two suture tails.

A second suture (for example, an Arthrex FiberTape® suture tape) is passed slightly anterior to the initial suture construct from deep to superficial medial to the rotator cable. The limb that has been passed is pulled through the tissue about three quarters of the full suture tape length, leaving one short and one long limb. The long limb of suture tape is again passed through the rotator cuff tissue from deep to superficial. A percutaneous portal is established for anchor insertion posteriorly just lateral to the acromion. Three limbs of suture are retrieved through the percutaneous portal, leaving only the long limb from the second suture behind, before preparing a socket to accept the implant. The three suture tails are loaded into a suture anchor (for example, Arthrex 4.75-mm BioComposite SwiveLock® anchor) and inserted under tension into the prepared socket to reestablish the posterior rotator cable attachment. The remaining suture tails can be cut through the percutaneous portal.

Returning to the lateral portal, the remaining long limb of suture is passed medial to the rotator cable in a circumferential running baseball stitch configuration until reaching the anterior limit of the defect. With each pass, the suture is pulled tight to remove any slack. A second suture tape (for example, Arthrex FiberTape® suture tape) is used for additional reinforcement of the anterior cable by completing a SpeedFix™ configuration with each free limb of suture, leaving a total of three suture tails at the anterior cable insertion site. A second percutaneous portal is established anteriorly for insertion of the final anchor. The three suture limbs are pulled through the anterior percutaneous portal and loaded into a suture anchor (for example, Arthrex 4.75-mm BioComposite SwiveLock® anchor). A socket is prepared at the anatomic location of the anterior rotator cable and the anchor is inserted with the sutures under tension.

Exemplary Surgical Steps—Summary

1 Diagnostic intraarticular arthroscopy is performed through a standard posterior portal to identify disruption of the rotator cable attachments anteriorly and posteriorly.

2 Arthroscope is moved to the subacromial space through a posterolateral portal where bursectomy and evaluation of the rotator cuff tear and tissue quality is performed to confirm an irreparable tear.

3 A suture anchor is placed at the anterior cable attachment loaded with three limbs of high strength suture tape.

4 Suture tape is passed in a continuous running or locking baseball stitch configuration from anterior to posterior through rotator cuff tissue medial to the rotator cable and lateral to the musculotendinous junction.

5 At the posterior cable attachment, the suture tapes are anchored through a suture anchor to the insertion site of the posterior cable on the greater tuberosity.

The technique of the present disclosure reduces suture pull through the rotator cuff tendon by stitching up the rotator cable and then anchoring down with two or more fixation devices such as anchors at the far lateral ends of the rotator cable, where the rotator cable would naturally attach to the bone. The technique offers anchor points at the cable insertion sites and a continuous stitch that reinforces the rotator cable. The technique offers an improved way to repair large soft tissue tears where only certain attachment points are fixated back to bone (in contrast to current techniques where soft tissue that tears off of bone is typically repaired by placing suture anchors in bone, the sutures are passed through tissue, and all of the tissue is fixated back to bone). The tissue between the attachment points is reinforced with a suture in different configurations.

Advantages of the disclosed technique are as follows:
Utilization of suture tape reinforcement on the rotator cable yields minimal morbidity risk;
Reconstruction of the rotator cable adds biomechanical strength to the overall construct;
Reconstruction of the rotator cable reduces tear propagation;
Reconstruction technique can be performed on rotator cuff tendon tears (including retracted rotator cuff tendon tears); and
Standard postoperative rotator cuff repair rehabilitation protocols can be followed.

As the rotator cable is a big fibrous bundle with dense collagen fibers, the rotator cable carries the applied forces to the rotator cuff tendon like a "suspension bridge." Rotator cuff tendon tears that involve the rotator cable tend to progress (i.e., tear) more rapidly. By reinforcing the rotator cable with a continuous suture stitch and with anchors at the two cable insertion sites (and an optional reinforcement material), the anatomic footprint is restored with enhanced management of torn rotator cuff tissue and advanced healing.

The rotator cable reconstruction disclosed herein confers the following benefits:
Reconstruct the cable insertion sites using anchors and reinforce cable with running stitch;
FiberTape® suture tape passed multiple times around rotator cable from anterior-posterior and/or posterior-anterior;
Suture method with locking/reinforced suture passes at anterior and posterior cable attachments;
Suture passing method through and around rotator cable to bridge cable footprint points to displace forces from the rotator cuff tendon; and
1 anchor posterior and 1-2 anchors anterior.

FIGS. 8 and 9 illustrate schematic representations of reinforced rotator cable 199 which is provided with multiple fixation devices 60a1, 60a2 at either the anterior site or the posterior site (anterior or posterior cable insertion points), to reinforce rotator cable 50. The number of fixation devices employed at either site depends on the degree of the tear, dimensions and characteristics of the rotator cable, and surgeon's preference, among others.

In an exemplary embodiment, reconstruction of the rotator cable may be conducted by employing fixation devices, wherein at least one of the fixation devices is a soft anchor or an "all-suture" anchor. A soft anchor (soft suture anchor or all-suture soft knotless anchor) is provided with a soft anchor sleeve (sheath or tubular member) with two open ends, and at least two flexible shuttling strands extending through the soft anchor sleeve (sheath). The flexible strands may extend through the sleeve in similar or different directions and/or orientations and/or locations. The flexible tubular sleeve with the shuttling strands may be secured into or onto bone, and flexible strands may pass over soft tissue (rotator cable) and are secured into bone to approximate soft tissue to bone. Details of an exemplary soft suture anchor with a soft anchor sleeve (sheath or tubular member) and flexible shuttling strands are set forth, for example, in U.S. Pat. No. 10,849,734 issued Dec. 1, 2020, entitled "Methods of Tissue Repairs," the disclosure of which is incorporated by reference in its entirety herein.

A knotless, tensionable, reinforced rotator cable construct 99, 199 includes a stitched region 55 formed with a flexible coupler 10 passed at least once around rotator cable 50 and secured at its natural insertion points 1, 2 with at least one fixation device 60a, 60a1, 60a2, 60b. The flexible coupler 10 may be any strand, thread, fiber, yarn or similar structure, or plurality of such structures, that allows stitching around the perimeter of the rotator cable and along at least a length of the rotator cable 50. The at least one fixation device 60a, 60a1, 60a2, 60b can be an anchor, implant, screw, button, plate, or any device that allows attachment of the flexible coupler 10 of the reinforced cable construct 99, 199 to bone. The fixation device 60a, 60a1, 60a2, 60b can be formed of metal, biocomposite polymers, PEEK materials, or can be an "all-suture soft anchor."

A surgical assembly for rotator cable reinforcement comprises a flexible coupler 10 for knotless attachment to a rotator cable 50; at least two fixation devices 60a, 60a1, 60a2, 60b attached to the flexible coupler; and optionally, a reinforcement material attached to the rotator cable 50. At least one of the at least two fixation devices 60a, 60a1, 60a2, 60b is a knotless suture anchor.

A method of forming a knotless, locking, tensionable, reinforced rotator cable construct 99, 199 comprises inter alia the steps of: (i) suturing or stitching rotator cable 50 with at least one flexible coupler 10 to form a reinforced rotator cable 99, 199; and (ii) securing the at least one flexible coupler 10 in a knotless manner. In an embodiment, the step of (ii) securing the at least one flexible coupler 10 in a knotless manner occurs before the step of (i) suturing or stitching rotator cable 50 with at least one flexible coupler 10. In an embodiment, the step of (ii) securing the at least one flexible coupler 10 in a knotless manner occurs after the step of (i) suturing or stitching rotator cable 50 with at least one flexible coupler 10. The flexible coupler can be secured with at least one fixation device 60a, 60a1, 60a2, 60b. The at least one fixation device 60a, 60a1, 60a2, 60b may be an anchor, implant, screw, button, or plate. The at least one fixation device 60a, 60a1, 60a2, 60b may be a knotless suture anchor. The step of suturing or stitching rotator cable 50 includes passing the flexible coupler 10 with a suture passer 40 around the rotator cable 50 multiple times to form at least one complete loop of suture around the rotator cable 50 and as part of suturing/stitched region 55. In an embodiment, the flexible coupler is passed multiple times to form a suturing/stitched region 55 of a knotless suturing repair that provides for faster tissue reduction with a stronger and more reproducible repair. The method may further include the step of (iii) providing a reinforcement/reinforcing material to augment the final repair. Step (iii) may occur before step (i).

Flexible coupler 10 can be formed of any suture, tape, weave, fabric, ribbon, textile, web, or mesh, or any combinations of these materials. Flexible coupler 10 can be braided or multi-filament suture such as FiberTape® suture tape (as disclosed in U.S. Pat. No. 7,892,256, the disclosure of which is incorporated in its entirety herewith) or collagen tape, or wide "tape like" material, or combinations thereof. Flexible coupler 10 can be formed of a high strength suture material such as FiberWire® suture, sold by Arthrex, Inc. of Naples, Fla., and described in U.S. Pat. No. 6,716,234, the disclosure of which is incorporated by reference herein. FiberWire® suture is formed of an advanced, high-strength fiber material, namely ultrahigh molecular weight polyethylene (UHMWPE), sold under the tradenames Spectra®

(Honeywell International Inc., Colonial Heights, Va.) and Dyneema® (DSM N.V., Heerlen, the Netherlands), braided with at least one other fiber, natural or synthetic, to form lengths of suture material. Flexible coupler 10 can be formed of any material or combination of materials that can be provided on a rotator cable, along a length thereon, and stitched/sutured to provide additional fixation when the rotator cable is further secured. The flexible coupler 10 may be absorbable or non-absorbable.

Flexible coupler 10 can consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. Flexible coupler 10 can consist of strands with cross-sections of various forms and geometries, including round, oval, rectangular, or flat, among others, or combinations of such forms and geometries. In an embodiment, at least one of flexible coupler 10 and reinforcement material can be provided as a suture which is braided, knitted or woven.

Flexible coupler 10 can be also formed of a stiff material, or combination of stiff and flexible materials, depending on the intended application. Flexible coupler 10 can be also coated and/or provided in different colors. In an embodiment, parts (or all) of surgical construct 99, 199 can be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture and/or tape, pliability, handleability or abrasion resistance, for example.

Flexible coupler 10 can be also provided with tinted tracing strands, or otherwise contrast visually with other parts of the construct, which remain a plain, solid color, or displays a different tracing pattern, for example. Various structural elements of surgical construct 99, 199 may be visually coded, making identification and handling of the suture legs simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A method of rotator cable reinforcement comprising:
reinforcing a native rotator cable of a rotator cuff tendon having two natural insertion points, wherein the reinforcing is conducted by forming a series of stitching loops along at least one dimension of the rotator cable with at least one flexible coupler, to form a reinforced rotator cable; and
securing the flexible coupler to bone without tying knots.

2. The method of claim 1, wherein the at least one flexible coupler is suture or suture tape.

3. The method of claim 1, wherein the series of stitching loops are formed with a suture passer and around the rotator cable.

4. The method of claim 1, wherein the series of stitching loops are formed with a suture passer and around and through the rotator cable.

5. The method of claim 1, wherein the reinforcing is conducted by:
securing the at least one flexible coupler to a first fixation device;
securing the first fixation device at a first location in the greater tuberosity;
attaching the at least one flexible coupler to a suture passing instrument;
forming a plurality of suture passes around a perimeter of the rotator cable and along a length extending between a first natural insertion point of the rotator cable and a second natural insertion point of the rotator cable, to form a reinforced rotator cable;
attaching the at least one flexible coupler to a second fixation device; and
securing the second fixation device at a second location in the greater tuberosity.

6. The method of claim 5, wherein the first location in the greater tuberosity corresponds to the first natural insertion point of the rotator cable, and the second location in the greater tuberosity corresponds to the second natural insertion point of the rotator cable.

7. The method of claim 5, wherein the first fixation device is a knotless anchor.

8. The method of claim 5, wherein the second fixation device is a knotless anchor.

9. The method of claim 1, wherein securing the flexible coupler to bone without tying knots comprises attaching the flexible coupler to at least one knotless fixation device and securing the at least one knotless fixation device in the greater tuberosity.

10. The method of claim 1, further comprising providing a reinforcement material attached to the rotator cable, and between the rotator cable and the flexible coupler.

11. The method of claim 10, wherein the reinforcement material is a tape, a ribbon, a weave, a mesh, or combination of tape, ribbon, weave, or mesh.

12. The method of claim 10, wherein at least one of the flexible coupler and the reinforcement material is bioabsorbable.

* * * * *